United States Patent
Church et al.

(10) Patent No.: US 9,766,255 B2
(45) Date of Patent: Sep. 19, 2017

(54) BIOSENSORS ENGINEERED FROM CONDITIONALLY STABLE LIGAND-BINDING DOMAINS

(71) Applicants: President and Fellows of Harvard College, Cambridge, MA (US); University of Washington, Seattle, WA (US)

(72) Inventors: George M. Church, Brookline, MA (US); Justin Feng, Cambridge, MA (US); Daniel J. Mandell, Brookline, MA (US); David Baker, Seattle, WA (US); Stanley Fields, Seattle, WA (US); Benjamin Ward Jester, Seattle, WA (US); Christine Elaine Tinberg, Seattle, WA (US)

(73) Assignees: President and Fellows of Harvard College, Cambridge, MA (US); University of Washington, Seattle, WA (US)

( * ) Notice: Subject to any disclaimer, the term of this patent is extended or adjusted under 35 U.S.C. 154(b) by 0 days.

(21) Appl. No.: 14/993,509

(22) Filed: Jan. 12, 2016

(65) Prior Publication Data

US 2016/0202256 A1  Jul. 14, 2016

Related U.S. Application Data

(60) Provisional application No. 62/102,378, filed on Jan. 12, 2015.

(51) Int. Cl.
*C12N 7/00* (2006.01)
*G01N 33/74* (2006.01)

(52) U.S. Cl.
CPC ....... *G01N 33/743* (2013.01); *G01N 2500/10* (2013.01)

(58) Field of Classification Search
None
See application file for complete search history.

(56) References Cited

PUBLICATIONS

Tinberg et al. (Nature 2013 vol. 501, p. 212-216, including Materials and Methods total 7 pages).*
Wang et al. (PNAS 1994 vol. 91, p. 8180-8184).*
Miyazaki et al. (J. Am. Chem. Soc. 2012 vol. 134, p. 3942-3945).*
Shoulders et al. (J. Am Chem. Soc. 2013 vol. 135, p. 8129-8132).*
Tang et al. (J. American Chem Soc 2013, vol. 135, p. 10099-10103).*

* cited by examiner

*Primary Examiner* — Jacob Cheu
(74) *Attorney, Agent, or Firm* — Banner & Witcoff, Ltd.

(57) ABSTRACT

Disclosed is a biosensor engineered to conditionally respond to the presence of specific small molecules, the biosensors including conditionally stable ligand-binding domains (LBDs) which respond to the presence of specific small molecules, wherein readout of binding is provided by reporter genes or transcription factors (TFs) fused to the LBDs.

18 Claims, 5 Drawing Sheets

BIOSENSORS ENGINEERED FROM CONDITIONALLY STABLE LIGAND-BINDING DOMAINS

RELATED APPLICATIONS

This application claims priority from U.S. provisional patent application No. 62/102,378, filed Jan. 12, 2015, which is hereby incorporated herein by reference in its entirety for all purposes.

STATEMENT OF GOVERNMENT INTERESTS

This invention was made with government support under HDTRA-1-10-1-0040 and N-00024-10-D-6318/0024 awarded by U.S. Department of Defense, and under DE-FG02-02ER63445 awarded by U.S. Department of Energy, and under GM103533 awarded by National Institutes of Health. The government has certain rights in the invention.

FIELD

Embodiments of the present disclosure relate in general to a biosensor that includes ligand binding domains (LBDs) engineered to conditionally respond to the presence of specific small molecules, the biosensors including LBDs which are fused to reporter proteins or transcription factors (TFs).

BACKGROUND

Small molecules play important roles across a diversity of biological processes, yet methods for detecting their abundance and activity in living cells are lacking. Common methods for detecting proteins, such as genetic fusion to FRET reporters, N. Mochizuki et al., Nature 411, 1065 (Jun. 28, 2001), to peptides that ligate to chemical probes, G. Gaietta et al., Science 296, 503 (Apr. 19, 2002), or to protein complementation fragments, C. D. Hu, T. K. Kerppola, Nat Biotechnol 21, 539 (May, 2003), are typically inapplicable to the detection of small molecules.

Some metabolite binding proteins undergo dramatic conformational rearrangements upon complex formation with target molecules, so that genetic fusion to FRET pairs or labeling with environmentally sensitive dyes are natural routes to detection, R. Y. Tsien, S. A. Hires, Y. L. Zhu, Proc Natl Acad Sci USA 105, 4411 (Mar. 18, 2008). However, this approach is limited to the minority of well-characterized cases exhibiting allosteric transduction of small-molecule binding events.

Other techniques such as the SNAP, M. A. Brun, K. T. Tan, E. Nakata, M. J. Hinner, K. Johnsson, J Am Chem Soc 131, 5873 (Apr. 29, 2009), and HaloTag, G. V. Los et al., ACS Chem Biol 3, 373 (Jun. 20, 2008), methods involve covalent fusion of target analogs to environmentally-sensitive fluorescent tags that self-label to reporter protein complexes. High target concentrations then compete away the lower affinity analogs causing a shift in reporter fluorescence. Although, in principle, these strategies offer modular approaches to small molecule detection, they require in vitro synthesis with membrane impermeable compounds, prohibiting their use in vivo, R. H. Newman, M. D. Fosbrink, J. Zhang, Chem Rev 111, 3614 (May 11, 2011).

SUMMARY

The present disclosure provides biosensors engineered from conditionally stable ligand-binding domains. These biosensors are prepared by using a general, modular approach to engineer proteins that sense small molecule localization and abundance in vivo, and couple the response to a detectable behavior, response, reaction or process, which may include fluorescence, catalysis, signaling, gene transcription or protein expression (FIG. 1).

Biosensors engineered to respond conditionally to the presence of specific small molecules would be useful tools with which, e.g., to detect environmental contaminants, modulate gene regulation, and select modifications to metabolic pathways that increase bioproduction yields, efficiencies or rates. Such biosensors are constructed here by two methods.

In the first method, mutations are introduced to a ligand binding domain (LBD) that render the LBD conditionally stable upon the presence of the cognate small molecule. The LBD is directly fused to a reporter protein, so that the destabilized LDB and reporter are rapidly cleared from the cell in the absence of the small molecule.

In the second method, a wild-type or conditionally stable LBD of the first method is placed within a scaffold including a DNA-binding domain and transcriptional activation domain (transcription factor, or TF) that activates expression of a reporter gene. Incorporation of a conditionally stable ligand-binding domain into the TF scaffold generates a destabilized TF that is quickly cleared from the cell and drives only a low level of reporter gene expression. Addition of the cognate ligand stabilizes the ligand-binding domain and increases in vivo levels of the TF, thus coupling transcriptional activation to the level of the small molecule. Relative to the first method that uses a LBD fused directly to a reporter protein, the TF-based system of the second method should be more sensitive and have a wider dynamic range at the expense of a rapid response time.

Several fusion constructs were created and tested, each minimally encoding a small molecule binding domain fused to a transcription factor or other reporter protein.

In one such construct, an engineered digoxigenin-binding protein, DIG10.3, was fused to the DNA-binding domain of Gal4 and a VP16 activation domain, and demonstrated the function of this sensor in S. cerevisiae.

Though the initial sensor was capable of inducing reporter expression in the presence of digoxigenin, FACS analysis of a library of DIG10.3 variants allowed the identification of mutants that enhanced induction by several-fold.

Deletion of the ABC transporter Pdr5 enhanced the sensitivity of the sensor by restricting efflux and increasing intracellular levels of exogenously added ligand. Further mutations were introduced to alter the sensor's substrate specificity to prefer progesterone.

Two of the mutations that increase sensitivity were found by randomly mutagenizing the entire DNA binding domain/LBD/transcriptional activation domain construct (R60S and L77F). In this case, the mutations reside in the DNA binding domain. Degron sequences have also been fused to these constructs to further destabilize them in some embodiments.

Lastly, the new sensor was used to detect the biosynthesis of progesterone in yeast. This approach should be generally applicable to small molecules for which a binding protein either exists or can be designed.

Aspects of the present disclosure include methods of using in vivo protein-based small molecule biosensors of the present disclosure for monitoring or visualizing concentration and localization of small molecules. Small molecule-mediated protein degradation functions well in both the cytosol and the nucleus, M. A. Sellmyer, L. C. Chen, E. L. Egeler, R. Rakhit, T. J. Wandless, PLoS One 7, e43297

(2012), so intracellular dynamics may be monitored. For example, retinoic acid (RA) plays an important role in stem cell differentiation, and this role may depend on the translocation of RA from the cytosol to the nucleus, T. T. Schug, D. C. Berry, N. S. Shaw, S. N. Travis, N. Noy, Cell 129, 723 (May 18, 2007). Sensors for RA would enable to probe the local dynamics of RA before, during, and after stem cell differentiation.

Aspects of the present disclosure include methods for the regulation of cellular processes, including feedback sensors to regulate gene expression across biosynthesis pathways. Bottleneck compounds in metabolic pathways can be toxic. For example, farnesyl pyrophosphate (FPP) is a critical precursor in many terpene biosynthetic pathways, including for biofuels. FPP is toxic at high concentrations, but nearly-toxic levels are optimal for high product yield. Biosensors for intermediates like FPP coupled to transcriptional regulators of upstream enzymes like FPP synthase could maintain production near optimal levels. See P. P. Peralta-Yahya, F. Zhang, S. B. del Cardayre, J. D. Keasling, Nature 488, 320 (Aug. 16, 2012).

Aspects of the present disclosure include methods of using sensor-selectors to optimize pathway production. Sensors for biosynthetic products can be coupled to selectable markers to allow directed evolution for strain optimization. For example, flavonoids are a class of small molecule metabolites with a variety of impacts on human health, R. M. van Dam, N. Naidoo, R. Landberg, Current Opinion in Lipidology 24, 25 (February 2013). Cells containing sensors for flavonoids coupled to antibiotic resistance markers or metabolite production would evolve into strains that increase flavonoid production when challenged by antibiotics or media lacking auxotrophy metabolites.

Aspects of the present disclosure include methods of using additional reporters to monitor hormones and drugs, and direct control of enzyme catalysis or cell signaling proteins like GTPases and kinases.

Aspects of the present disclosure include methods of using sensors for extracellular compounds like toxins and environmental contaminants for in vivo detection and response for bioremediation, biomining, biosafety, and regulation of microbial communities.

Aspects of the present disclosure include methods of using proteins containing clinically relevant mutations for diseases related to protein misfolding placed within the disclosed system as sensors to screen for small molecules that rescue folding and function of the clinically relevant destabilized proteins.

Prior methods for sensing proteins, such as fusion to FRET reporters, N. Mochizuki et al., Nature 411, 1065 (Jun. 28, 2001), to peptides that ligate to chemical probes, G. Gaietta et al., Science 296, 503 (Apr. 19, 2002), or to protein complementation fragments, C. D. Hu, T. K. Kerppola, Nat Biotechnol 21, 539 (May, 2003), typically cannot be applied to small molecules because small molecules cannot be genetically encoded. Alternative small-molecule sensing methods like SNAP, M. A. Brun, K. T. Tan, E. Nakata, M. J. Hinner, K. Johnsson, J Am Chem Soc 131, 5873 (Apr. 29, 2009), and HaloTag, G. V. Los et al., ACS Chem Biot 3, 373 (Jun. 20, 2008), can't be readily used in vivo because they require in vitro synthesis with membrane impermeable compounds. The current method is generalizable (almost all small molecules of interest bind proteins, and almost all proteins fold into a stable conformation), and modular (the interchangeable reporter repertoire is large, including fluorescent proteins, enzymes, transcriptional regulators, signaling proteins, and others). Methods that rely on conformational rearrangements of binding proteins, R. Y. Tsien, S. A. Hires, Y. L. Zhu, Proc Natl Acad Sci USA 105, 4411 (Mar. 18, 2008), are limited to the small subset of targets that induce such dramatic conformational changes, and cannot easily be made modular.

Specific embodiments of the disclosure include the following:

Embodiment 1

A biosensor including ligand binding domains (LBDs) engineered to conditionally respond to the presence of specific small molecules, the biosensors including LBDs which are fused to reporter proteins or transcription factors (TFs). In some embodiments, the LBD and the reporter or TF are genetically fused. In some embodiments, the components can be fused together post-translationally.

Embodiment 2 the biosensor of Embodiment 1, further including elements suitable for use as a tool for the detection of environmental contaminants.

Embodiment 3 the biosensor of Embodiment 1, further including elements suitable for use as a tool for gene regulation.

Embodiment 4 the biosensor of Embodiment 1, further including elements suitable for use as a tool for metabolic engineering.

Embodiment 5 the biosensor of Embodiment 1, further including a scaffold including a DNA-binding domain and transcriptional activation domain.

Embodiment 6 the biosensor of Embodiment 5 wherein the DNA binding domain or transcriptional activation domains are mutated to further destabilize the biosensor and increase response to the small molecule.

Embodiment 7 the biosensor of Embodiment 6 wherein a known degradation sequence tag is fused to the biosensor to further destabilize the biosensor and alter the response to the small molecule.

Embodiment 8 the biosensor of Embodiment 5, wherein ligand-induced stabilization of the TF activates expression of a reporter gene.

Embodiment 9 the biosensor of Embodiment 8, wherein incorporation of an unstable ligand-binding domain into the TF scaffold generates a destabilized protein that is quickly cleared from the cell and drives only a low level of reporter gene expression.

Embodiment 10 the biosensor of Embodiment 5, wherein addition of a cognate ligand stabilizes the ligand-binding domain and increases in vivo levels of the TF, thus coupling transcriptional activation to the level of the small molecule.

Embodiment 11 a biosensor including an engineered digoxigenin-binding protein, DIG10.3, fused to the DNA-binding domain of Gal4 and a VP16 activation domain.

Embodiment 12 the biosensor of Embodiment 11, which was capable of inducing reporter expression in the presence of digoxigenin.

Embodiment 13 the biosensor of Embodiment 11, further including DIG10.3 variants or mutants that enhanced induction by several-fold.

Embodiment 14 the biosensor of Embodiment 11, wherein deletion of an ABC transporter Pdr5, enhanced the sensitivity of the sensor by restricting efflux and increasing intracellular levels of exogenously added ligand.

Embodiment 15 the biosensor of Embodiment 11, wherein further mutations were introduced to alter the sensor's substrate specificity to prefer progesterone, whereby the biosensor was able to detect the biosynthesis of progesterone in yeast.

Embodiment 16 a method of detecting small molecules for which a binding protein either exists or can be designed including contacting a sample suspected of containing the small molecule with a biosensor of Embodiment 1.

Embodiment 17 a method of Embodiment 16 where the LBD responds conditionally to the presence of the small molecule because it has been mutated so that its stability depends on the presence of the small molecule.

It should be appreciated by those persons having ordinary skill in the art(s) to which the present disclosure relates that any of the features described herein in respect of any particular aspect and/or embodiment of the present disclosure can be combined with one or more of any of the other features of any other aspects and/or embodiments of the present disclosure described herein, with modifications as appropriate to ensure compatibility of the combinations. Such combinations are considered to be part of the present disclosure contemplated by this disclosure.

It is to be understood that both the foregoing general description and the following detailed description are exemplary and explanatory only and are not restrictive of the disclosure as claimed. Other embodiments will be apparent to those skilled in the art from consideration of the specification and practice of the disclosure disclosed herein.

DETAILED DESCRIPTION

Figure 1:
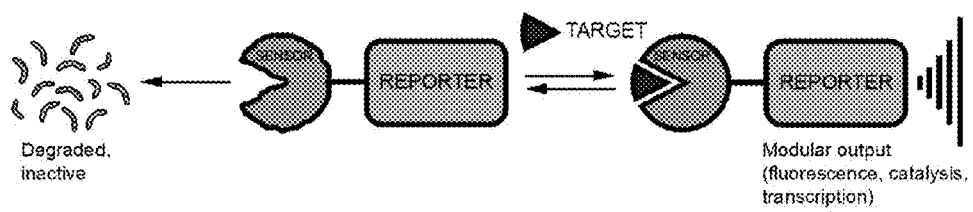
FIG. 1 is an illustration of a protein-based in vivo small molecule biosensor. A natural or engineered protein that binds a small molecule target is converted to a sensor by introducing destabilizing mutations. Destabilization of the sensor due to low target abundance induces degradation of the entire construct, creating a modular biosensor for the target.

Embodiments of the present disclosure are directed to a general, modular approach to engineer proteins that sense small molecule localization and abundance in vivo, and couple the response to cellular behavior, which may include fluorescence, catalysis, signaling, and gene transcription. The generalizability of this disclosure arises from its basis on two pervasive biophysical principles: molecular recognition and protein folding.

Embodiments of the present disclosure are directed to a biosensor that includes a ligand binding domain engineered to respond conditionally to the presence of specific small molecules, the biosensor also including a ligand binding domain that is fused to a reporter protein or transcription factor. According to one aspect, the biosensor includes elements suitable for use as a tool for the detection of environmental contaminants. According to another aspect, the biosensor includes elements suitable for use as a tool for gene regulation. According to another aspect, the biosensor includes elements suitable for use as a tool to select modifications to biosynthetic pathways that improve bioproduction yields, efficiencies, or rates. According to another aspect, the ligand binding domain and the reporter or transcription factor are genetically fused. According to another aspect, the components are fused together post-translationally.

According to one aspect, the biosensor further includes a scaffold including a DNA-binding domain and transcriptional activation domain. According to another aspect, the DNA binding domain or transcriptional activation domain of the biosensor is mutated to further destabilize the biosensor and increase response to the small molecule. According to another aspect, a known degradation sequence tag is fused to the biosensor to further destabilize the biosensor and alter the response to the small molecule. According to another aspect, ligand-induced stabilization of the transcription factor activates expression of a reporter gene in the biosensor that includes a scaffold as well as a DNA-binding domain and transcriptional activation domain.

According to one aspect, incorporation of an unstable ligand-binding domain into the transcription factor scaffold generates a destabilized protein that is more readily cleared from the cell than would be a biosensor with a stable ligand binding domain. According to another aspect, addition of a cognate ligand stabilizes the ligand-binding domain and increases in vivo levels of the transcription factor, thus coupling transcriptional activation to the level of the small molecule.

Embodiments of the present disclosure are directed to a biosensor that includes an engineered digoxigenin-binding protein, DIG10.3, fused to the DNA-binding domain of Gal4 and a VP16 activation domain. According to one aspect, the biosensor is capable of inducing reporter expression in the presence of digoxigenin. According to another aspect, the biosensor includes DIG10.3 variants or mutants that enhance induction by several-fold. According to another aspect, deletion of an ABC transporter Pdr5, enhances the sensitivity of the sensor by restricting efflux and increasing intracellular levels of exogenously added ligand. According to another aspect, further mutations are introduced to alter the sensor's substrate specificity to prefer progesterone, whereby the biosensor is able to detect the biosynthesis of progesterone.

Embodiments of the present disclosure are directed to a method of detecting small molecules for which a binding protein either exists or can be designed that includes contacting a sample suspected of containing the small molecule with a biosensor that includes a ligand binding domain engineered to respond conditionally to the presence of specific small molecules and a ligand binding domain that is fused to a reporter protein or transcription factor. According to one aspect, the ligand binding domain responds conditionally to the presence of the small molecule because it has been mutated so that its stability depends on the presence of the small molecule.

According to one aspect, sensors are constructed in two exemplary ways. The first method of constructing a sensor is by fusing a ligand binding domain (LBD) to a reporter or other protein, mutagenizing the LBD, and screening or selecting for LBDs exhibiting conditional stability in the presence or absence of ligand; and the second method of constructing a sensor is by attaching a wild-type or conditionally destabilized LBD to a transcription factor (TF) in order to afford greater control over sensor response.

To build a sensor by the first method, mutations are introduced to an existing LDB that binds the target, which is genetically fused to a reporter protein (FIG. 1). The construct can be inducibly or constitutively expressed. In the absence of its small molecule target, the LBD is destabilized and tagged for proteasome-mediated degradation. Due to the processivity of the proteasome, the entire construct is then degraded, abrogating the reporter signal. Introduction of the target small molecule stabilizes the LBD and rescues reporter function. As a result, the level of reporter activity depends on local target concentration. In principle any genetically encodable polypeptide can serve as the modular reporter, and the only requirement for construction is the existence of a LBD.

The starting LBD sequence can either come from a naturally occurring binding protein or can be designed in silico. In silico designs can produce physiologically orthogonal binding proteins for ligands lacking a suitable natural LBD. See C. E. Tinberg et al., Nature 501, 212 (Sep. 12, 2013). Thus, sensors built using this approach have few prerequisites, and once engineered can be fused to various reporters in a modular fashion, for example switching from fluorescence for screening and imaging to a transcription factor for regulating a metabolic pathway. Further, since the requisite ubiquitin proteasome system is highly conserved throughout eukaryotes, sensors engineered in one eukaryotic organism will likely be portable to others.

Figure 2:
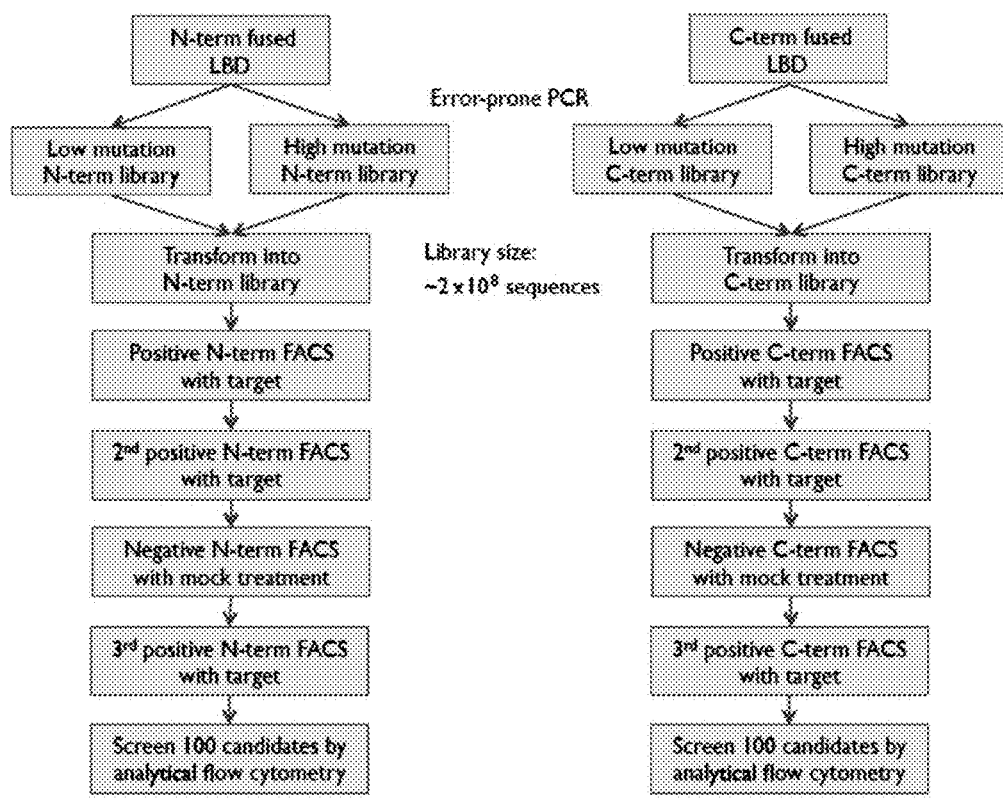
FIG. 2 is an illustration of a process for constructing protein-based small molecule biosensors by error-prone PCR and FACS sorting.

As proof of principle, sensors for the chemotherapeutic trimethoprim (TMP) in S. cerevisiae were engineered. Sensors were constructed from E. coli dyhydrofolate reductase (EcDHFR), which naturally binds TMP at low nanomolar affinity. EcDHFR was genetically fused to a yeast-enhanced GFP reporter, and subjected to error-prone PCR followed by multiple rounds of FACS sorting (FIG. 2).

Figure 3:
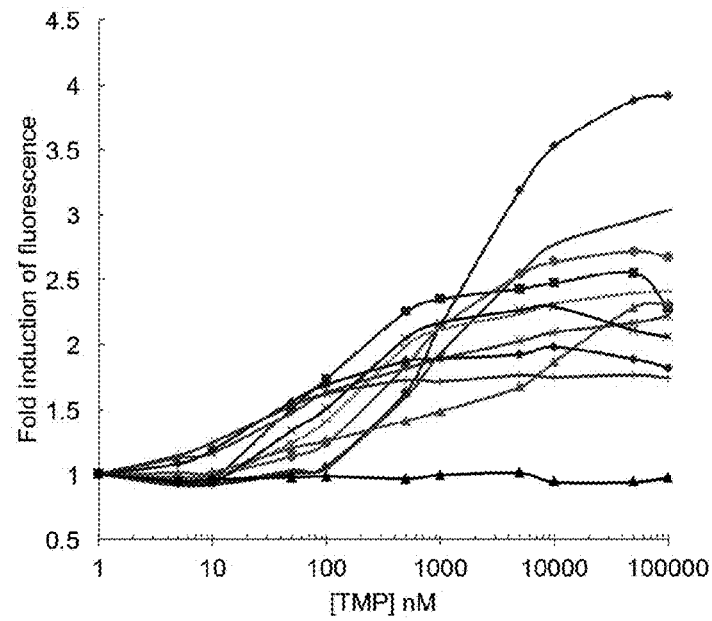
FIG. 3 graphically shows data from EcDHFR-based sensors for TMP in yeast constructed by error-prone PCR and FACS sorting. Black triangles are background fluorescence from untransformed cells. The process produces a set of constructs with a range of responses to TMP.

By screening for cells that showed high-fluorescence in the presence of TMP, but low fluorescence in the absence of TMP, the mutants of EcDHFR were produced that function as sensors for TMP in yeast (FIG. 3). This approach is similar in construction to the "degradation domains" engineered by the Wandless lab for mammalian cells at Stanford, L. A. Banaszynski, L. C. Chen, L. A. Maynard-Smith, A. G. Ooi, T. J. Wandless, Cell 126, 995 (Sep. 8, 2006). However, those constructs failed to show sensitivity when ported to yeast cells, R. Rakhit, S. R. Edwards, M. Iwamoto, T. J. Wandless, Bioorg Med Chem Lett, (Jun. 16, 2011).

In addition to developing sensors derived from natural ligand-binding proteins, the ability to use computationally designed proteins to create novel biosensors has been demonstrated. Computational design has been used to engineer a LBD (DIG10.3) for the sterol digoxigenin with high affinity and selectivity, C. E. Tinberg et al., Nature 501, 212 (Sep. 12, 2013). Further, key mutations in the binding pocket can switch binding specificity from digoxigenin to other compounds. For example, the mutations Y34F/Y99F/Y101F (hereafter referred to as DIG10.3FFF) alter binding specificity from digoxigenin to progesterone.

Figure 4:
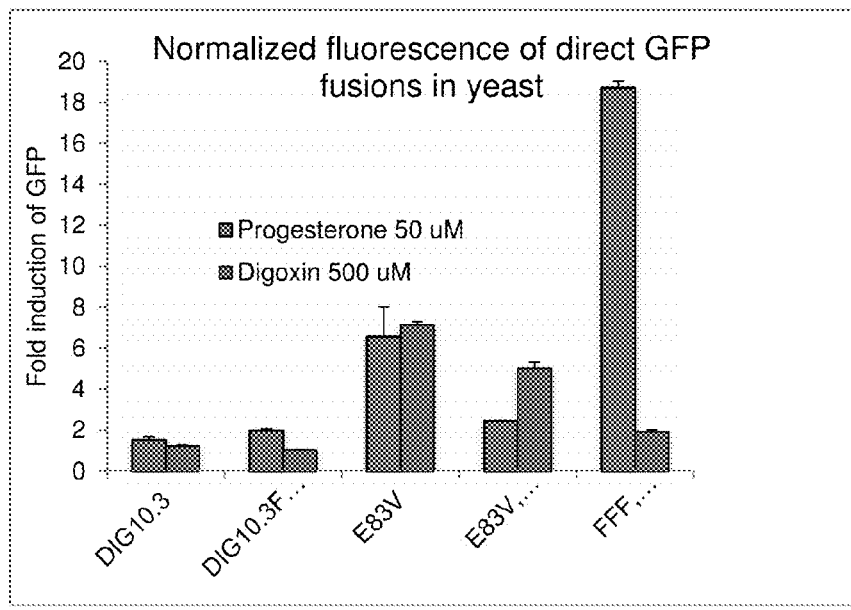
FIG. 4 illustrates the sensitivity and selectivity measurements of DIG10.3-based biosensors for digoxigenin and progesterone fused to GFP and expressed in yeast. Digoxin, a glycoside of digoxigenin found to bind DIG10.3 with similar affinity as its aglycone, is used.

Using the previously described error-prone PCR and FACS sorting strategy, mutants of DIG10.3 and DIG10.3FFF were produced that are responsive to intracellular concentrations of digoxin and progesterone respectively (FIG. 4). The novel progesterone biosensor (DIG10.3FFF H9R, F15G, I64F, A92T) exhibits high sensitivity to progesterone as well as selectivity against digoxigenin. The digoxigenin biosensor (DIG10.3 E83V) exhibits poor selectivity against progesterone, but additional mutations (DIG10.3 E83V/G17A) have been identified that increase specificity at a slight cost to overall dynamic range (FIG. 4).

To build a sensor by the second method, a LBD is attached to a TF. The TF can consist of either a native transcriptional regulator or an engineered TF comprised of a DNA-binding domain (DBD) and a transcriptional activation domain (TAD). By fusing a LBD to the TF, transcriptional activity is controlled by the presence or absence or ligand. This strategy has been previously used to engineer a □-estradiol-dependent TF in *S. cerevisiae* from human steroid LBDs, J. F. Louvion, B. Havaux-Copf, D. Picard, Gene 131, 129 (Sep. 6, 1993). Through its constituent parts the TF sensor can be engineered to bind to the promoter region of a gene of interest, usually either an endogenous gene or a recombinant reporter, and drive its transcription.

As with the direct reporter fusion, the LBD binding to its cognate small molecule results in stabilization of the entire protein, decreased degradation, and an increase in reporter activity. In contrast with attaching the LBD directly to the reporter, the TF construct affords an increase to the dynamic range of the sensor at the expense of a rapid response.

Figure 5:
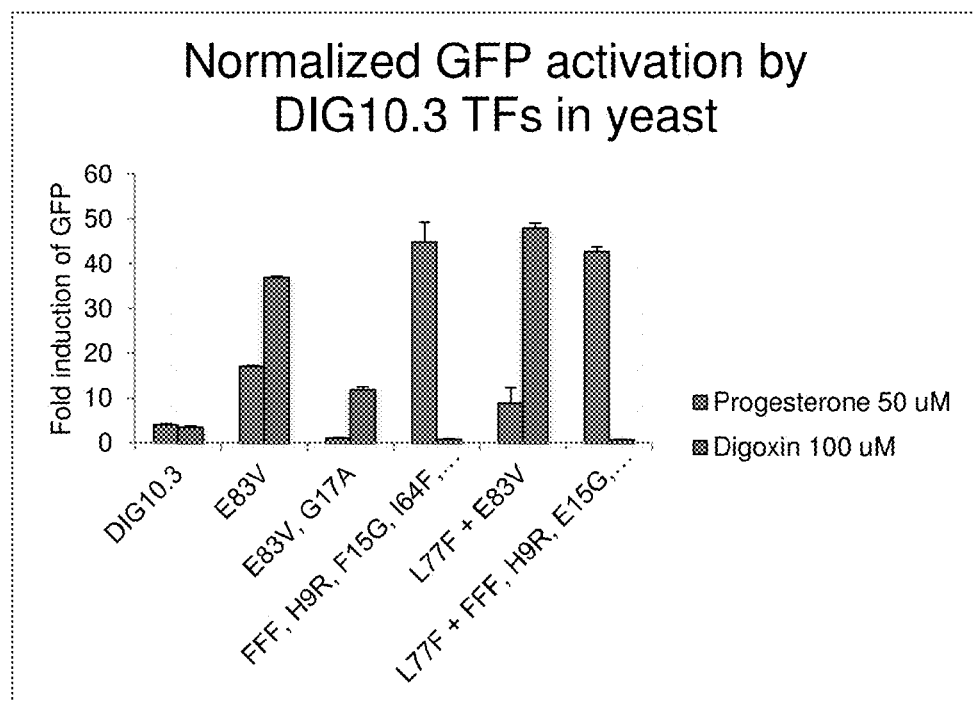
FIG. 5 illustrates the sensitivity and selectivity measurements of DIG10.3-based biosensors for digoxigenin and progesterone fused to Gal4 and Vp16 and expressed in yeast.

To demonstrate this approach, DIG10.3 was cloned as a fusion to the DBD of Gal4 and a virally-derived TAD, VP16, generating GDVP. Due to an inherent instability in DIG10.3, the initial GDVP construct exhibited a several fold increase in reporter expression when cells were treated with exogenous digoxigenin (FIG. 5, DIG10.3). To increase dynamic range, destabilizing mutations were introduced into the TF-based sensors using the same procedure outlined in FIG. 2.

Figure 6:
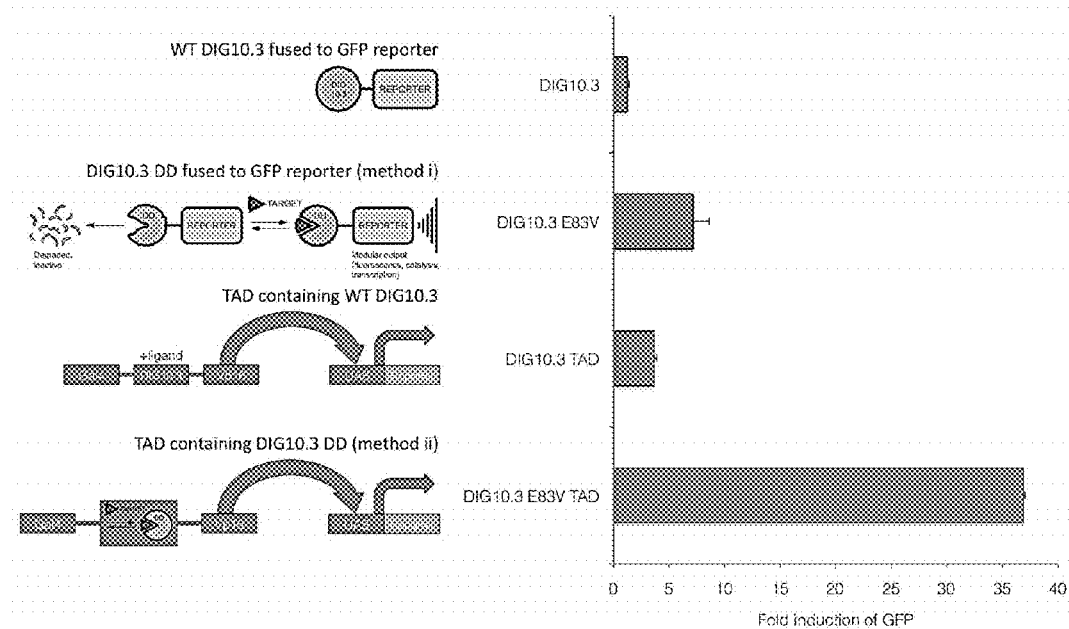
FIG. 6 is a comparison of DIG DD sensors as direct fusions to GFP reporter or contained within TAD construct.
Figure 7:
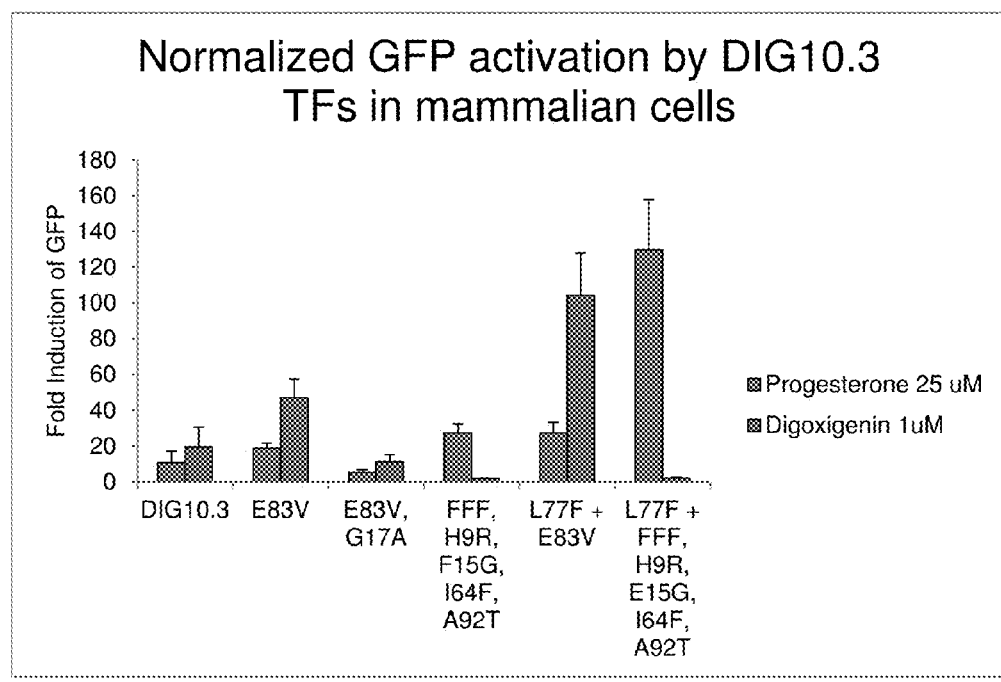
FIG. 7 illustrates the sensitivity and selectivity measurements of DIG10.3-based biosensors for digoxigenin and progesterone fused to Gal4 and Vp16 and expressed in HEK-293 mammalian cells.

Both the digoxigenin and progesterone binding DIG10.3 variants identified in the direct reporter fusion screen were found to similarly improve the performance of the TF-based sensor (FIG. 5). Random mutagenesis of the entire TF scaffold allowed the identification of mutations in the Gal4 DBD (R60S and L77F) that further enhanced the fold induction of the sensors by reducing TF activity under non-permissive conditions (FIG. 5, L77F columns). Sensors constructed by this method can show improved response in comparison to the first method alone (FIG. 6). Further, these sensors are effective when ported to mammalian cells, and can even demonstrate improved response (FIG. 7).

It is to be understood that the embodiments of the present disclosure which have been described are merely illustrative of some of the applications of the principles of the present disclosure. Numerous modifications may be made by those skilled in the art based upon the teachings presented herein without departing from the true spirit and scope of the disclosure. The contents of all references, patents and published patent applications cited throughout this application are hereby incorporated by reference in their entirety for all purposes.

The following examples are set forth as being representative of the present disclosure. These examples are not to be construed as limiting the scope of the disclosure as these and other equivalent embodiments will be apparent in view of the present disclosure, figures, tables, and accompanying claims.

Example I

Construction of DIG10.3 Variants for Conditionally Stable Digoxigenin and Progesterone LBDs General considerations—digoxigenin was purchased from Sigma Aldrich (St. Louis, Mo.) and was used as received.

The DIG10.3 sequence was cloned by Gibson assembly, D. G. Gibson et al., Nat Methods 6, 343 (May, 2009), into a pUC19 plasmid containing yeast enhanced GFP (yEGFP) and a KanMX6 cassette flanked by 1000 and 500 bp upstream and downstream homology to the HO locus. The DIG10.3 sequence was randomized by error-prone PCR using a Genemorph II kit from Agilent Technologies. An aliquot containing 100 ng of target DNA (423 bp out of a 7.4 kb plasmid) was mixed with 5 µl of 10× Mutazyme buffer, 1 µl of 40 mM dNTPS, 1.5 µl of 20 µM forward and reverse primer containing 90 bp overlap with the pUC19 plasmid (oJF70 and oJF71), and 1 µl of Mutazyme polymerase in 50 µl. The reaction mixture was subject to 30 cycles with Tm of 60° C. and extension time of 1 min. Sanger sequencing of 16 colonies showed a mutation rate of 0-7 mutations/kb. Vector backbone was amplified using Q5 polymerase (NEB) with oJF76 and oJF77 primers with Tm of 65° C. and extension time of 350 min. Both PCR products were isolated by 1.5% agarose gel electrophoresis and the randomized target was inserted as a genetic fusion to yeGFP by Gibson assembly. Assemblies were pooled, washed by ethanol precipitation, and resuspended in 50 µl dH2O, which was drop dialyzed (Millipore) and electroporated into *E. cloni* supreme cells (Lucigen). The library was expanded in culture and maxiprepped (Qiagen) to 500 µg/µl aliquots. 16 µg of library was drop dialyzed and electrotransformed into yeast strain Y7092 for homologous recombination into the HO locus. Integrants were selected by growth on YPAD solid media containing G418 followed by outgrowth in YPAD liquid media containing G418.

Example II

Sorting and Screening of Digoxigenin and Drogesterone LDB Fusions to yeGFP

Yeast libraries were subject to three rounds of fluorescence activated sorting in a BD FACSAria IIu. For the first round, cells were grown overnight to an OD600 of ~1.0 in YPAD containing sterol (500 µM digoxigenin or 50 µM progesterone), and cells showing the upper 5% of fluorescence activation were collected and expanded overnight to an OD600 of ~1.0 in YPAD lacking sterol. In the second sort, cells displaying the lowest ~3% fluorescence activation were collected. Cells passing the second round were passaged overnight in YPAD containing sterol to an OD600 of ~1.0 and sorted once more for the upper 5% of fluorescence activation. The sorted libraries were expanded in YPAD liquid culture and plated on solid YPAD media. 96 colonies from each library were clonally isolated and grown overnight in deep well plates containing 500 µl of YPAD. Candidates were diluted 1:50 into two deep well plates with SE-complete media: one plate supplemented with sterol and the other with DMSO vehicle. Cells were grown for another 4 h, and then diluted 1:3 into microtitre plates of 250 µl of the same media. Candidates were screened by analytical flow cytometry on a BD LSRFortessa cell analyzer. The forward scatter, side scatter, and GFP fluorescence (530 nm band pass filter) were recorded for a minimum of 20,000 events. FlowJo X software was used to analyze the flow cytometry data. The fold induction was calculated by normalizing mean GFP fluorescence activation for each sterol to the mean GFP fluorescence in the DMSO only control. Highest induction candidates were subject to Sanger sequencing with primers flanking the LBD sequence.

Example III

Reporter Plasmid Construction and Integration

Reporter genes were cloned into the integrative plasmid pUG6, U. Guldener, S. Heck, T. Fielder, J. Beinhauer, J. H. Hegemann, Nucleic Acids Res 24, 2519 (Jul. 1, 1996), using the Gibson method. Each reporter (either yEGFP or firefly luciferase) was cloned to include a 5' Gall promoter (*S. cerevisiae* Gall ORF bases (−455)-(−5)) and a 3' Cyc terminator. Linearized PCR cassettes containing both the reporter and an adjacent KanMX antibiotic resistance cassette were generated using primers containing 50 bp flanking sequences of homology to the Ura3 locus. Integrative PCR product was transformed into the yeast strain PJ69-4a using the Gietz method, R. D. Gietz, R. H. Schiestl, Nat Protoc 2, 38 (2007), to generate integrated reporter strains.

Example IV

Gal4-DIG10.3-VP Plasmid Construction

Gal4-DIG10.3-VP16 fusion constructs were prepared using the Gibson cloning method. Constructs were cloned into the plasmid p416CYC (p16C), D. Mumberg, R. Muller, M. Funk, Gene 156, 119 (Apr. 14, 1995). Gal4 (residues 1-93, UniProt ID PO4386), DIG10.3, and VP16 (residues 363-490, UniProt ID P06492) PCR products for were amplified from their respective templates using Phusion high-fidelity polymerase (NEB, Waltham, Mass.) and standard PCR conditions (98° C. 10 s, 60° C. 20 s, 72° C. 30 s; 30 cycles). The 8 residue linker sequence GGSGGSGG (SEQ ID NO:1) was used between Gal4 and DIG10.3. PCR primers were purchased from Integrated DNA technologies and contained 24-30 5' bases of homology to either neighboring fragments or plasmid. Clones containing an N-terminal degron were similarly cloned fusing residues 1-67 of Mat-alpha2 (UniProt ID POCY08) to the 5'-end of Gal4-DIG10.3-VP16. Plasmids were transformed into yeast using the Gietz method, R. D. Gietz, R. H. Schiestl, Nat Protoc 2, 38 (2007), with transformants being plated on synthetic complete media lacking uracil (SC-ura).

Example V

Gal4-DIG10.3-VP Mutant Construction

Mutations were introduced into DIG10.3/pETCON, C. E. Tinberg et al., Nature 501, 212 (September 12), or the appropriate Gal4-DIG10.3-VP construct using Kunkel mutagenesis, T. A. Kunkel, Proc Natl Acad Sci USA 82, 488 (January 1985). Oligos were ordered from Integrated DNA Technologies, Inc. For mutants constructed in pETCON/DIG10.3, the mutagenized DIG10.3 gene was amplified by 30 cycles of PCR (98° C. 10 s, 61° C. 30 s, 72° C. 15 s) using Phusion high-fidelity polymerase (NEB, Waltham, Mass.) and 5'- and 3'-primers having homologous overlap with the DIG10.3-flanking regions in p16C-GDVP64 (Gal4_DIG10.3_VP64_hr_fwd and Gal4_DIG10.3_VP64_hr_rev_rc). Genes were inserted into p16C-GDVP64 by Gibson assembly using vector digested with HindIII and EcoRI-HF.

Example VI

Gal4-DIG10.3-VP Progesterone Variant Construction

The genes for DIG10.3 Y34F, DIG10.3 Y101F, and DIG10.3 Y34F/Y99F/Y101F were amplified from the appropriate DIG10.3/pETCON construct, C. E. Tinberg et al., Nature 501, 212 (Sep. 12, 2013), by 30 cycles of PCR (98° C. 10 s, 59° C. 30 s, 72° C. 15 s) using Phusion high-fidelity polymerase (NEB, Waltham, Mass.) and 5'- and 3'-primers having homologous overlap with the DIG10.3- flanking regions in p16C-GDVP64 (DIG_fwd and DIG_rev). Genes were inserted into p16C-GDVP16 by Gibson assembly using p16C-Gal4-(HE)-VP16 vector digested with HindIII and EcoRI-HF.

Example VII

Gal4-DIG10.3-VP16 Error-prone Library Construction and Selections

A randomized Gal4-DIG10.3-VP16 library was constructed by error-prone PCR using a Genemorph II kit from Agilent Technologies. An aliquot containing 20 ng p16C GDVP16, 20 ng p16C GDVP16 E83V, and 20 ng p16C Y36H was mixed with 5 μL of 10× Mutazyme buffer, 1 μL of 40 mM dNTPS, 1.5 μL of 20 μM forward and reverse primer containing 37- and 42-bp overlap with the pl6C vector for homologous recombination, respectively (GDV_ePCR_fwd and GDV_ePRC_rev), and 1 μL of Mutazyme polymerase in 50 μL. The reaction mixture was subjected to 30 cycles of PCR (95° C. 30 s, 61° C. 30 s, 72° C. 80 s). Template plasmid was digested by adding 1 μL of DpnI to the reaction mixture and incubating for 3 hr at 37° C. Resulting PCR product was purified using a Quiagen PCR cleanup kit, and a second round of PCR was used to amplify enough DNA for transformation. Gene product was amplified by combining 100 ng of mutated template DNA with 2.5 μL of 10 μM primers (GDV_ePCR_fwd and GDV_ePR-C_rev), 10 μL of 5× Phusion buffer HF, 1.5 μL of DMSO, and 1 μL of Phusion high-fidelity polymerase (NEB, Waltham, Mass.) in 50 μL. Product was assembled by 30 cycles of PCR (98° C. 10 s, 65° C. 30 s, 72° C. 35 s). Following confirmation of a single band at the correct molecular weight by 1% agarose gel electrophoresis, the PCR product was purified using a Quaigen PCR cleanup kit and eluted in ddH$_2$O.

Example VIII

Yeast Strain PyE1 ΔPDR5 Transformation

Yeast strain PyE1 ΔPDR5 was transformed with 9 μg of amplified PCR library and 3 μg of p16C Gal4-(HE)-VP16 triply digested with SalI-HF, BamHI-HR, and EcoRI-HF using the method of Benatuil, L. Benatuil, J. M. Perez, J. Belk, C. M. Hsieh, Protein Eng Des Sel 23, 155 (April), yielding ~10$^6$ transformants. Following transformation, cells were grown in 150 mL of C-ura media supplemented with 2% glucose. Sanger sequencing of 12 individual colonies revealed an error rate of ~1-6 mutations per gene.

Cells were subjected to three rounds of cell sorting using a Cytopeia (BD Influx) fluorescence activated cell sorter. For the first round, cells displaying high fluorescence in the presence of DIG (on-state) were collected. Transformed cells were pelleted by centrifugation (4 min, 4000 rpm) and resuspended to a final OD$_{600}$ of 0.1 in 50 mL of C-ura media supplemented with 2% glucose, pen/step antibiotics, and 5 μM DIG prepared as a 100 mM solution in DMSO. The library was incubated at 30° C. for 9 h and then sorted. Cells displaying the highest fluorescent values in the GFP channel were collected (1,747,058 cells collected of 32,067,013 analyzed; 5.5%), grown up at 30° C. in C-ura, and passaged twice before the next sort. For the second round of sorting, cells displaying low fluorescence in the absence of DIG (off-state) were collected. Cells were pelleted by centrifugation (4 min, 4000 rpm) and resuspended to a final OD$_{600}$ of 0.1 in 50 mL of C-ura media supplemented with 2% glucose and pen/step antibiotics. The library was incubated at 30° C. for 8 h and then sorted. Cells displaying low fluorescent values in the GFP channel were collected (1,849, 137 cells collected of 22,290,327 analyzed; 11.1%), grown up at 30° C. in C-ura, and passaged twice before the next sort. For the last sorting round, cells displaying high fluorescence in the presence of DIG (on-state) were collected. Cells were prepared as for the first sort. Cells displaying the highest fluorescent values in the GFP channel were collected (359,485 cells collected of 31,615,121 analyzed; 1.1%). After the third sort, a portion of cells were plated and grown at 30° C. Plasmids from 12 individual colonies were harvested using a Zymoprep Yeast miniprep II kit (Zymo Research Corporation, Irvine, Calif.) and the gene was amplified by 30 cycles of PCR (98° C. 10 s, 52° C. 30 s, 72° C. 40 s) using Phusion high-fidelity polymerase (NEB, Waltham, Mass.) with the T3 and T7 primers. Sanger sequencing (Genewiz, Inc., South Plainfield, N.J.) was used to sequence each clone in the forward (T3) and reverse (T7) directions.

Example IX

Gal4-DIG10.3-VP16 Error-prone Library Mutation Screens

Of twelve sequenced clones from the library sorts, two showed significantly improved (>2-fold) response to DIG over the input clones (GDVP16_lib.3 and GDVP16_lib.6). GDVP16_lib.3 contains the following mutations: Gal4_T44T (silent), Gal4_L77F, DIG10.3_E5D, DIG10.3_E83V, DIG10.3_R108R (silent), DIG10.3_L128P, DIG10.3_I137N, DIG10.3_S143G, and VP16_A44T. GDVP16_lib.6 contains the following mutations: Gal4_R60S, Gal4_L84L (silent), VP16_G17G (silent), VP16_L48V, and VP16_H98H (silent). To identify which mutations led to the observed changes in DIG response, variants of these clones with no silent mutations and each individual point mutant were constructed using Kunkel mutagenesis, T. A. Kunkel, Proc Natl Acad Sci USA 82, 488 (January 1985). Oligos were ordered from Integrated DNA Technologies, Inc. Sequence-confirmed plasmids were transformed into PyE1 ΔPDR5, R. D. Gietz, R. H. Schiestl, Nat Protoc 2, 38 (2007), and plated onto selective C-ura media supplemented with 2% glucose. Individual colonies were inoculated into liquid media, grown at 30° C., and passaged once. Cells were pelleted by centrifugation (4 min, 1700×g) and resuspended to a final $OD_{660}$ of 0.1 in 1 mL of C-ura media supplemented with 2% glucose and 50 μM DIG prepared as a 100 mM solution in DMSO. Following a 6 hr incubation at 30° C., cells were pelleted, resuspended in 200 μL of PBS, and cellular fluorescence was measured on an Accuri C6 flow cytometer using a 488 nm laser for excitation and a 575 nm band pass filter for emission. FlowJo software version 7.6 was used to analyze the flow cytometry data. Data are given as the mean GFP fluorescence of the single yeast population in the absence of DIG (off-state) and the mean GFP fluorescence of the higher fluorescing yeast population in the presence of DIG (on-state).

Example X

Computational Model of Gal4-DIG10.3

A model of the Gal4-DIG10.3 fusion was built using Rosetta Remodel, P. S. Huang et al., PLoS ONE 6, e24109, to assess whether the linker between Gal4 and Dig10.3, which are both dimers, would allow for the formation of a dimer in the fusion construct. In the simulation, the Gal4 dimer was held fixed while the relative orientation of the DIG10.3 monomers were sampled symmetrically using fragment insertion in the linker region. Constraints were added across the DIG10.3 dimer interface to facilitate sampling. The lowest energy model satisfied the dimer constraints, indicating that a homodimer configuration of the fusion is possible.

Example XI

Specificity Assays

Yeast strains expressing the biosensor and GFP reporter (either genetically fused or able to be transcriptionally activated by the TAD) were grown overnight at 30° C. in synthetic complete media lacking uracil (SC-ura) supplemented with 2% glucose for 12 hours. Following overnight growth, cells were pelleted by centrifugation (5 min, 5250 rpm) and resuspended into 500 μl of SC-ura. 10 μl of the washed culture was resuspended into 490 μl of separately prepared media each containing a sterol of interest (SC-ura media supplemented with 2% glucose, the sterol of interest, and DMSO to a final concentration of 1% DMSO). Sterols were tested at a concentration of 100 μM digoxin, 50 μM progesterone, 250 μM pregnenolone, 100 μM digitoxigenin, 100 μM beta-estradiol, and 100 μM hydrocortisone. Stock solutions of sterols were prepared as a 50 mM solution in DMSO.

Resuspended cultures were then incubated at 30° C. for 8 hours. 125 μl of incubated culture was resuspended into 150 μl of fresh SC-ura media supplemented with 2% glucose, the sterol of interest, and DMSO to a final concentration of 1%. These cultures were then assayed by analytical flow cytometry on a BD LSRFortessa using a 488 nm laser for excitation. The forward scatter, side scatter, and GFP fluorescence (530 nm band pass filter) were recorded for a minimum of 20,000 events. FlowJo X software was used to analyze the flow cytometry data. The fold induction was calculated by normalizing mean GFP fluorescence activation for each sterol to the mean GFP fluorescence in the DMSO only control.

Example XII

Yeast Spotting Assays

Yeast strain PJ69-4a transformed with p16C plasmids containing degron-Gal4-DIG10.3-VP16 variants were first inoculated from colonies into SC-ura media supplemented with 2% glucose (SD-ura) and grown at 30 C overnight (16 h). 1 mL of each culture was pelleted by centrifugation (3000 rcf, 2 min), resuspended in 1mL of fresh SD-ura and the OD660 measured. Each culture was then diluted in SD-ura media to an OD660=0.2 and incubated at 30 C for 4-6 hrs. 1 mL of each culture was pelleted and resuspended in sterile, distilled water and the OD660 measured again. Each transformant was then diluted to an OD660=0.1. Four ⅒ serial dilutions of each culture was prepared in sterile water (for a total of 5 solutions). 10 μl of each dilution was spotted in series onto several SD agar plates lacking uracil and histidine and containing 3-aminotriazole (0, 1, or 10 mM). Plates were additionally prepared from 200× steroid solutions in DMSO (0.5% DMSO final in plates). Each spotting assay was performed by spotting transformants on a series of combinations of 3-aminotriazole and steroid concentrations.

Example XIII

Construction of K562 Cell Lines

The PiggyBac transposase system was employed to integrate biosensor constructs into K562 cells. Vector PB713B-1 (Systems Biosciences) was used a backbone. Briefly, this backbone was digested with NotI and HpaI and GalDBD-Biosensor-VP16, Gal4BS-Elb-eGFP, and sEF1-Puromycin were cloned in. GalDBD is the Gal DNA binding domain and Gal4BS represents the four copies of the binding sequence. For hCas9, the PiggyBac system was also employed, but the biosensors were directly fused to the N-terminal of Cas9 and were under control of the CAGGS (SEQ ID NO:2) promoter. Cas9 for *S. pyogenes* was used.

Example XIV

K562 GFP Screening Protocol

For each construct, 1 µg of the PiggyBac construct along with 400 ng of transposase were nucleofected into K562 cells using the Lonza Nucleofection system as per manufacturer settings. Two days post-transfection, cells underwent puromycin selection (2 ug/mL) for at least eight additional days to allow for unintegrated plasmid to dilute out and ensure all cells contained the integrated construct. An aliquot of 100,000 cells of each integrated population were then cultured with 25 µM of progesterone, 1 µM of digoxygenin, or no small molecule. Forty-eight hours after small molecule addition, cells were then analyzed using flow cytometry using the BD Biosciences Fortessa system. Mean GFP fluorescence of the populations were compared.

Example XV

K562 Cas9 Screening Protocol

Construct integration was performed exactly the same for the Cas9 experiments as for the GFP, except constructs were integrated into K562 cells which contained broken eGFP reporter construct. Briefly, introduction of an engineered nuclease along with a donor oligonucleotide can "fix" the eGFP and produce fluorescent cells. Upon successful integration ~10 days after initial transfection, 500,000 cells were then nucleofected with 500 ng of guide RNA (sgRNA) and 2 µg of donor oligonucleotide. Nucleofected cells were then collected with 200 µl of media and 50 µl aliquots were added to wells containing 950 µl media. Thus, each nucleofection could be split into four separate wells where each well could either contain 1 µM of digoxygenin, 25 µM of progesterone or no small molecule. Forty-eight hours later, cells were analyzed using flow cytometry and percentage of eGFP positive cells were compared.

The following references are cited herein, and to the extent necessary for a full understanding of the present disclosure, each of these references is hereby incorporated herein by reference in its entirety.

1. N. Mochizuki et al., Nature 411, 1065 (Jun. 28, 2001).
2. G. Gaietta et al., Science 296, 503 (Apr. 19, 2002).
3. C. D. Hu, T. K. Kerppola, Nat Biotechnol 21, 539 (May, 2003).
4. R. Y. Tsien, S. A. Hires, Y. L. Zhu, Proc Natl Acad Sci USA 105, 4411 (Mar. 18, 2008).
5. M. A. Brun, K. T. Tan, E. Nakata, M. J. Hinner, K. Johnsson, J Am Chem Soc 131, 5873 (Apr. 29, 2009).
6. G. V. Los et al., ACS Chem Biol 3, 373 (Jun. 20, 2008).
7. R. H. Newman, M. D. Fosbrink, J. Zhang, Chem Rev 111, 3614 (May 11, 2011).
8. M. A. Sellmyer, L. C. Chen, E. L. Egeler, R. Rakhit, T. J. Wandless, PLoS One 7, e43297 (2012).
9. T. T. Schug, D. C. Berry, N. S. Shaw, S. N. Travis, N. Noy, Cell 129, 723 (May 18, 2007).
10. P. P. Peralta-Yahya, F. Zhang, S. B. del Cardayre, J. D. Keasling, Nature 488, 320 (Aug. 16, 2012).
11. R. M. van Dam, N. Naidoo, R. Landberg, Current opinion in lipidology 24, 25 (February 2013).
12. C. E. Tinberg et al., Nature 501, 212 (Sep. 12, 2013).
13. L. A. Banaszynski, L. C. Chen, L. A. Maynard-Smith, A. G. Ooi, T. J. Wandless, Cell 126, 995 (Sep. 8, 2006).
14. R. Rakhit, S. R. Edwards, M. Iwamoto, T. J. Wandless, Bioorg Med Chem Lett, (Jun. 16, 2011).
15. J. F. Louvion, B. Havaux-Copf, D. Picard, Gene 131, 129 (Sep. 6, 1993).
16. D. G. Gibson et al., Nat Methods 6, 343 (May, 2009).
17. U. Guldener, S. Heck, T. Fielder, J. Beinhauer, J. H. Hegemann, Nucleic Acids Res 24, 2519 (Jul. 1, 1996).
18. R. D. Gietz, R. H. Schiestl, Nat Protoc 2, 38 (2007).
19. D. Mumberg, R. Muller, M. Funk, Gene 156, 119 (Apr. 14, 1995).
20. C. E. Tinberg et al., Nature 501, 212 (September 12).
21. T. A. Kunkel, Proc Natl Acad Sci USA 82, 488 (January 1985).
22. L. Benatuil, J. M. Perez, J. Belk, C. M. Hsieh, Protein Eng Des Sel 23, 155 (April).
23. P. S. Huang et al., PLoS ONE 6, e24109.
24. For a related patent document see, US Patent Pub. No. 2009-0215169 A1 entitled "Method for regulating protein function in cells using synthetic small molecules." Cooper G M, Nickerson D A, Eichler E E. Mutational and selective effects on copy-number variants in the human genome. Nat Genet. 2007 July; 39(7 Suppl):522-9.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A biosensor comprising a destabilized ligand binding domain (LBD), the LBD is conditionally stabilized upon binding to a cognate ligand, wherein the LBD is fused to a scaffold including a DNA-binding domain and a transcriptional activation domain, and wherein the DNA binding domain or the transcriptional activation domain is mutated to further destabilize the biosensor and increase response to the ligand.

2. The biosensor of claim 1, wherein the biosensor can be used for the detection of environmental contaminants.

3. The biosensor of claim 1, wherein the biosensor can be used for gene regulation.

4. The biosensor of claim 1, wherein the biosensor can be used to select modifications to biosynthetic pathways that improve bioproduction yields, efficiencies or rates.

5. The biosensor of claim 1 wherein a known degradation sequence tag is fused to the biosensor to further destabilize the biosensor and alter the response to the ligand.

6. The biosensor of claim 1, wherein ligand-induced stabilization of the biosensor activates expression of a reporter gene.

7. The biosensor of claim 6, wherein the destabilized biosensor is more readily cleared from the cell than the biosensor stabilized with the ligand.

8. The biosensor of claim 1, wherein addition of the cognate ligand stabilizes the LBD and increases in vivo levels of the LBD fusion protein, thus coupling transcriptional activation to the level of the ligand.

9. A biosensor comprising a destabilized digoxigenin-binding protein variant, DIG10.3 variant, fused to a Gal4 DNA-binding domain and a VP16 activation domain, wherein the DIG10.3 variant is stabilized upon binding to digoxigenin or progesterone.

10. The biosensor of claim 9, which is capable of inducing reporter expression in the presence of digoxigenin or progesterone.

11. The biosensor of claim 10, wherein the DIG10.3 variant enhances induction by several-fold.

12. The biosensor of claim 9, wherein the biosensor is able to detect the biosynthesis of progesterone.

13. A method of detecting a ligand for which a binding protein either exists or can be designed comprising contacting a sample suspected of containing the ligand with the biosensor of claim 1.

14. The method of claim 13, where the LBD responds conditionally to the presence of the ligand because it has been mutated so that its stability depends on the presence of the ligand.

15. The biosensor of claim 1, wherein the LBD and the DNA binding domain and the transcriptional activation domain are genetically fused.

16. The biosensor of claim 1, wherein the LBD and the DNA binding domain and the transcriptional activation domain are fused together post-translationally.

17. The biosensor of claim 1, wherein the ligand is a small molecule.

18. The method of claim 13, wherein the ligand is a small molecule.

* * * * *

UNITED STATES PATENT AND TRADEMARK OFFICE
CERTIFICATE OF CORRECTION

PATENT NO. : 9,766,255 B2
APPLICATION NO. : 14/993509
DATED : September 19, 2017
INVENTOR(S) : George M. Church et al.

It is certified that error appears in the above-identified patent and that said Letters Patent is hereby corrected as shown below:

In the Specification

Column 1, Line 14: under STATEMENT OF GOVERNMENT INTERESTS

Please delete:
"This invention was made with government support under HDTRA-1-10-1-0040 and N-00024-10-D-6318/0024 awarded by U.S. Department of Defense, and under DE-FG02-02ER63445 awarded by U.S. Department of Energy, and under GM103533 awarded by National Institutes of Health. The government has certain rights in the invention."

And insert:
-- This invention was made with Government support under GM103533 awarded by the National Institutes of Health, HDTRA1-10-1-0040 awarded by the Department of Defense, N00024-10-D-6318/0024 awarded by the Naval Sea Systems Command, and DE-FG02-02ER63445 awarded by the Department of Energy. The Government has certain rights in this invention. --

Signed and Sealed this
Twenty-seventh Day of February, 2018

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial
<220> FEATURE:
<223> OTHER INFORMATION: Residue linker sequence

<400> SEQUENCE: 1

Gly Gly Ser Gly Gly Ser Gly Gly
1               5

<210> SEQ ID NO 2
<211> LENGTH: 5
<212> TYPE: PRT
<213> ORGANISM: Artificial
<220> FEATURE:
<223> OTHER INFORMATION: Cas9 promoter

<400> SEQUENCE: 2

Cys Ala Gly Gly Ser
1               5
```